(12) United States Patent
Blin et al.

(10) Patent No.: US 8,110,206 B2
(45) Date of Patent: Feb. 7, 2012

(54) COSMETIC COMPOSITION COMPRISING A HYDROCARBON OIL AND A SILICONE OIL

(75) Inventors: Xavier Blin, Paris (FR); Véronique Ferrari, Maisons-Alfort (FR)

(73) Assignee: L'Oreal S.A., Paris (FR)

( * ) Notice: Subject to any disclaimer, the term of this patent is extended or adjusted under 35 U.S.C. 154(b) by 1045 days.

(21) Appl. No.: 10/656,146

(22) Filed: Sep. 8, 2003

(65) Prior Publication Data

US 2004/0126350 A1 Jul. 1, 2004

Related U.S. Application Data

(60) Provisional application No. 60/410,955, filed on Sep. 17, 2002.

(30) Foreign Application Priority Data

Sep. 6, 2002 (FR) ..................... 02 11095

(51) Int. Cl.
*A61K 8/02* (2006.01)
(52) U.S. Cl. ....................................... 424/401
(58) Field of Classification Search ............... 424/63, 424/64, 401
See application file for complete search history.

(56) References Cited

U.S. PATENT DOCUMENTS

| | | | |
|---|---|---|---|
| 5,928,652 A | 7/1999 | Bodelin-LeComte | |
| 5,961,998 A * | 10/1999 | Arnaud et al. | 424/401 |
| 6,592,855 B1 * | 7/2003 | Willemin et al. | 424/70.1 |
| 6,649,173 B1 | 11/2003 | Arnaud et al. | |
| 2001/0031269 A1 * | 10/2001 | Arnaud | 424/401 |
| 2002/0015714 A1 | 2/2002 | Agostini et al. | |
| 2002/0034526 A1 | 3/2002 | Agostini et al. | |
| 2002/0034528 A1 | 3/2002 | Agostini et al. | |
| 2002/0058054 A1 | 5/2002 | Arnaud | |
| 2003/0017124 A1 * | 1/2003 | Agostini et al. | 424/63 |
| 2003/0039621 A1 | 2/2003 | Arnaud et al. | |

FOREIGN PATENT DOCUMENTS

| | | |
|---|---|---|
| EP | 0 407 205 A2 | 1/1991 |
| EP | 0 819 419 A1 | 1/1998 |
| EP | 1 068 854 | 1/2001 |
| EP | 1 086 945 | 3/2001 |
| EP | 1 112 734 A2 | 7/2001 |
| EP | 1 184 028 A1 | 3/2002 |
| EP | 1 249 223 A1 | 10/2002 |
| EP | 1 249 226 A1 | 10/2002 |
| FR | 2 745 493 | 9/1997 |
| FR | 2 756 174 | 5/1998 |
| FR | 2 756 176 | 5/1998 |
| FR | 2 771 628 | 6/1999 |
| FR | 2 823 103 | 10/2002 |
| JP | 61 210018 A | 9/1986 |
| JP | H09-241130 | 9/1997 |
| JP | H10-158118 | 6/1998 |
| JP | 2002-322020 | 11/2002 |
| JP | 2003-34616 | 2/2003 |
| WO | WO 93/23008 | 11/1993 |
| WO | WO 02/47031 | 6/2002 |

OTHER PUBLICATIONS

"Specialist Surfactants," D. Robb ed., 1997, pp. 209-263, chapter 8 by P. Terech.
Derwent Publications Ltd., London, GG; AN 1986-287936 XP002246654 & JP 61 210018 A (Shiseido) Sep. 18, 1986.
Derwent Abstract for FR 277162B, Jun. 4, 1999.
Derwent Abstract for EP 1 068 854, Jan. 17, 2001.
Derwent Abstract for EP 1 086 945, Mar. 28, 2001.
French Search Report, Jul. 7, 2003.
European Search and Examination Report for EP 06 30 0700 (European counterpart to the present application), Nov. 14, 2006.

* cited by examiner

*Primary Examiner* — Michael G Hartley
*Assistant Examiner* — James Rogers
(74) *Attorney, Agent, or Firm* — Finnegan, Henderson, Farabow, Garrett & Dunner LLP

(57) ABSTRACT

The present disclosure relates to a composition comprising in a physiologically acceptable medium at least one phenylsilicone oil of high viscosity and at least one non-volatile hydrocarbon oil having a molecular mass of more than 500 g/mol. The composition possesses at least one good property chosen from staying power, gloss, and comfort.

47 Claims, No Drawings

COSMETIC COMPOSITION COMPRISING A HYDROCARBON OIL AND A SILICONE OIL

The present application claims benefit of U.S. Provisional Application No. 60/410,955, filed Sep. 17, 2002.

The present disclosure relates to a cosmetic composition comprising, in a physiologically acceptable medium, at least one high-viscosity phenylsilicone oil, at least one non-volatile hydrocarbon oil, at least one rheological agent, and at least one particulate phase. This composition may be in the form of a care or makeup composition for the skin, both of the human face and of the human body, including the scalp, lips or exoskeletal appendages of human beings, such as the hair, eyelashes, eyebrows or nails. The composition as disclosed herein possesses notable cosmetic properties, such as staying power, and gives the makeup or care product properties of gloss and/or comfort.

The composition as presently disclosed may be in the form of a makeup product for keratin materials (e.g., skin, lips, and exoskeletal appendages), possibly having non-therapeutic treatment and/or care properties. For example, the composition may be in the form of a lipstick, lip gloss, foundation, loose or compacted powder, blusher, eyeshadow, makeup base, concealer, tattooing product, mascara, eyeliner, nail varnish, artificial tanning product, and haircare or hair colouring product.

The use of silicone compounds in cosmetic compositions, such as makeup compositions, is familiar to formulators. Mention may be made, for example, of EP-A-0407205, which describes a composition comprising the combination of a silicone gum and a silicone oil that has good staying power, spread and comfort properties. For instance, this combination imparts excellent sensorial properties to cosmetic compositions, such as a non-greasy feel, spreading properties, and lubricity properties, and can allow a particularly homogeneous film to be obtained on the skin.

Also known is the use of silicone compounds for the purpose of increasing the staying power of cosmetic compositions, for example makeup. The problems of poor staying power are characterized by a change in colour (colour change, fade) generally as a result of interaction with sebum and/or perspiration secreted by the skin, in the case of foundation and rouge, or of interaction with the saliva in the case of lipsticks. These problems can require the user to apply fresh makeup at frequent intervals, which may constitute a loss of time.

However, silicone compounds may sometimes cause formulating problems, for instance, difficulties of dispersing pigments into the compositions comprising silicone media, thereby giving rise to poor development of the hue of the composition and to a granular appearance, which discourages the consumer from using this type of product, and which is unfavourable to the production of a glossy composition.

But there are numerous cosmetic compositions for which the gloss properties of the deposited film, following application to the keratin materials (skin, lips, exoskeletal appendages), are very important. Mention may be made, for example, of lipsticks, eyeshadows, nail varnishes, and certain hair products.

FR 2 771 628 describes the use of a silicone gum in solution in a phenyltrimethicone oil in a cosmetic composition. This gum has the advantage of being soluble with the oils commonly used in cosmetics.

EP 1 112 734 describes a transfer-resistant composition comprising a hydrocarbon oil and a silicone oil, which are insoluble in one another. The composition further comprises a volatile solvent.

In order to enhance the gloss it is known among formulators to use oils having a high viscosity and a high refractive index, such as oily polymers, for instance polybutenes or certain vegetable oils (castor oil for example). However, these compounds do not make it possible to obtain a film of a composition whose staying power, for example in terms of the gloss, is sufficient to last throughout the day.

It has been found, surprisingly, that the use of the combination of at least one high-viscosity phenylsilicone oil and at least one non-volatile hydrocarbon oil, which are soluble or dispersible in one another, makes it possible to obtain a composition that exhibits good cosmetic and/or sensorial properties, for example properties of staying power over time, and also properties of gloss and comfort. Additionally, such a composition may not irritate keratin materials.

The present disclosure provides a cosmetic composition comprising, in a physiologically acceptable medium, at least one phenylsilicone oil having a viscosity greater than or equal to 500 cSt and at least one non-volatile hydrocarbon oil having a molecular mass of more than 500 g/mol, wherein the composition has an average gloss of more than 100 out of 200 and a post-trial staying power of more than 40 out of 100.

The average gloss is measured with the aid of a gloss meter, conventionally, by the following method. A Leneta contrast chart referenced Form 1A Penopac is spread with a 50 μm layer of the composition whose average gloss is to be evaluated, using an automatic spreader. The layer covers at least the white background of the chart. The gloss is then measured immediately at 20° on the white background using a Byk Gardner microTri-Gloss gloss meter. The gloss of the composition can also be measured one hour after the composition has been applied.

The average gloss of the composition, measured at the time of application, can be, for example, greater than 120, 130, 140, 150 out of 200, such as 160 out of 200.

The average gloss of the composition measured one hour after application can be greater than 120 out of 200, and, for further example, 130 out of 200.

The post-trial staying power of the composition disclosed herein can be evaluated as follows on a group of at least 10 persons. The reduced diffusion index of incident light on the lips on which the cosmetic composition may be applied is measured on every person with a film camera. The mean of the ten measurements is calculated. The measurement conditions are described in patent application FR0207108, which content is incorporated herein by reference. Each person then applies his or her lips on a paper tissue. The reduced diffusion index of incident light on the lips with make-up is measured again, and the mean of measures is calculated. The persons involved in evaluating the staying power drink a hot drink and then a glass of water and eat four bites of sandwich and half an apple. The reduced diffusion index of incident light on the lips with make-up, after this meal, is measured. The mean of the measurements is then calculated.

The post-trial staying power is expressed as a percentage of a) the difference between the reduced diffusion index of the lips with make-up, after the meal, and the reduced diffusion index of the naked lips before applying the make-up, and of b) the difference between the reduced diffusion index of the lips with make-up, before the meal, and the reduced diffusion index of the naked lips.

The post-trial staying power of the composition according to the present disclosure is greater than 40 out of 100, for example greater than 50 out of 100.

The present disclosure also provides a cosmetic composition comprising, in a physiologically acceptable medium a) at least one phenylsilicone oil having a viscosity greater than or equal to 500 cSt, b) at least one non-volatile hydrocarbon oil which is soluble or dispersible in the said silicone oil and has a molecular mass of more than 500 g/mol, and c) at least one rheological agent, wherein the rheological agent is a silicone wax.

The present disclosure further provides a cosmetic composition comprising, in a physiologically acceptable medium a) at least one phenylsilicone oil having a viscosity greater than or equal to 500 cSt, b) at least one non-volatile hydrocarbon oil having a molecular mass of more than 600 g/mol, and c) a particulate phase, provided that the particulate phase comprises less than 5% of a volatile oil.

The present disclosure additionally provides a cosmetic composition comprising, in a physiologically acceptable medium, at least one phenylsilicone oil having a viscosity greater than or equal to 500 cSt and at least one non-volatile hydrocarbon oil having a molecular mass of more than 600 g/mol, the said hydrocarbon oil being soluble or dispersible in the said silicone oil.

The present disclosure likewise provides for the use of the combination of at least one phenylsilicone oil with a high viscosity greater than or equal to 500 cSt and at least one non-volatile hydrocarbon oil having a molecular mass of more than 600 g/mol which is soluble or dispersible in the said silicone oil in a composition comprising a physiologically acceptable medium, the said composition having properties of staying power and of gloss.

The present disclosure likewise provides for the use of the combination of at least one high-viscosity phenylsilicone oil and at least one non-volatile hydrocarbon oil having a molecular mass of more than 600 g/mol, which is soluble or dispersible in the said silicone oil, in a composition comprising a physiologically acceptable medium, as an agent for imparting staying power and/or gloss and/or comfort to the composition.

The present disclosure further provides a cosmetic method of imparting properties of staying power and/or gloss and/or comfort to a film of a cosmetic composition, which comprises introducing into the composition an effective amount of at least one high-viscosity phenylsilicone oil and at least one non-volatile hydrocarbon oil having a molecular mass of more than 600 g/mol, and which is soluble or dispersible in the said silicone oil.

"Physiologically acceptable" means non-toxic and capable of being applied to the skin (including the inside of the eyelids), the lips or the exoskeletal appendages of human beings.

"At least one" compound means one or more compounds.

"Oil" means any non-aqueous medium which is liquid at ambient temperature (25° C.) and atmospheric pressure (760 mm Hg).

A "non-volatile" compound is a compound capable of remaining on the skin or lips for a number of hours. A non-volatile compound has, for example, a non-zero vapour pressure, at ambient temperature and atmospheric pressure, of less than 0.02 mm Hg (2.66 Pa).

A "volatile" compound is a compound capable of evaporating from the skin or lips in less than an hour. A volatile compound can be selected from, for example, compounds having a vapour pressure, at ambient temperature and atmospheric pressure, of from 0.02 mm to 300 mm Hg (2.66 Pa to 40 000 Pa), for example from 0.1 to 90 mm Hg (13 Pa to 12 000 Pa).

A "high-viscosity" phenylsilicone oil is an oil having a viscosity of at least 500 cSt at 25° C. measured according standard ASTM D-445. The silicone oil is suitably not a silicone gum. The high-viscosity phenylsilicone oil may have a viscosity at 25° C., for example, ranging from 500 to 10 000 cSt, such as from 600 to 5 000 cSt, and further for example from 600 to 3 000 cSt.

The composition according to the present disclosure may further comprise a low-viscosity phenylsilicone oil, which has a viscosity of less than 500 cSt at 25° C. measured according to standard ASTM D-445. The low-viscosity phenylsilicone oil suitably has a viscosity at 25° C., for example, ranging from 5 to 499 cSt, for instance from 5 to 300 cSt, and further, for example, from 5 to 100 cSt.

The high-viscosity phenylsilicone oil and the low-viscosity phenylsilicone oil (if present) may be, for example, a phenyltrimethicone, a phenyldimethicone, a phenyltrimethylsiloxydiphenylsiloxane, a diphenyldimethicone, a diphenylmethyldiphenyltrisiloxane or a mixture of different phenylsilicone oils, and may, for example, correspond to the following formula (A):

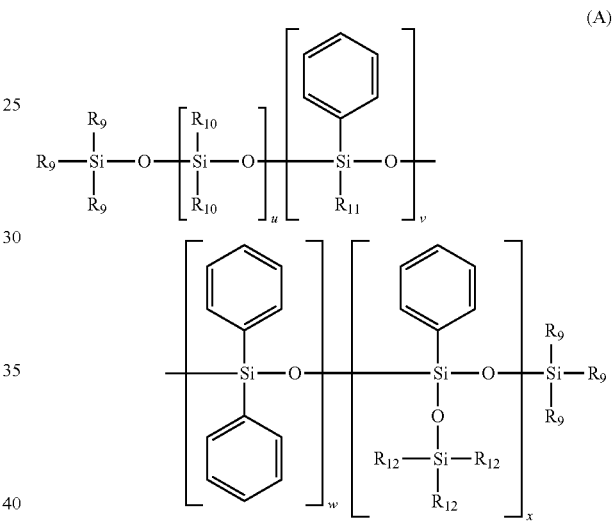

wherein:
$R_9$ and $R_{12}$, which may be identical or different, are chosen from a $C_1$-$C_{30}$ alkyl radical, an aryl radical, and an aralkyl radical, $R_{10}$ and $R_{11}$, which may be identical or different, are chosen from a $C_1$-$C_{30}$ alkyl radical and an aralkyl radical, u, v, w and x, which may be identical or different, are integers ranging from 0 to 900, with the provisos that the sum v+w+x is other than 0, and that the sum u+v+w+x ranges from 1 to 900; for example, u+v+w+x ranges from 1 to 800.

For further example, v is 0.

The low-viscosity phenylsilicone oil may, for example, satisfy the formula (A) with the sum u+v+w+x ranging from 1 to 150 and, for example, from 1 to 100, or even from 1 to 50, and the high-viscosity phenylsilicone oil may satisfy the formula (A) with sum u+v+w+x ranging from 151 to 900, for example from 160 to 800, or even from 160 to 500.

For example, the low-viscosity phenylsilicone oil may satisfy the following formula (B):

(B)

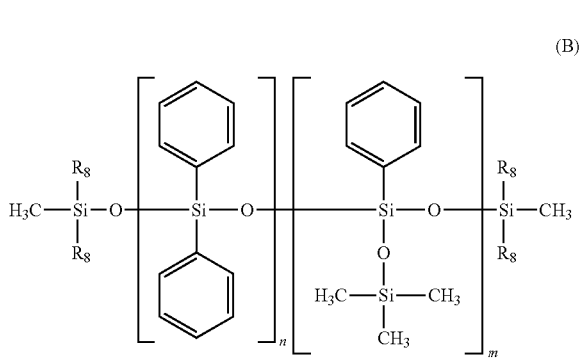

wherein:
R$_8$ is chosen from a C$_1$-C$_{30}$ alkyl radical, an aryl radical, and an aralkyl radical,
n is an integer ranging from 0 to 100, for example less than 100,
m is an integer ranging from 0 to 100, for example less than 100,
with the proviso that the sum m+n ranges from 1 to 100 and, for example, is less than 100.

High-viscosity phenylsilicone oils which can be used in accordance with the present disclosure include the oils 15 M 30 from PCR (500 cSt) or Belsil PDM 1000 (1 000 cSt) from Wacker. The values in parenthesis represent viscosities at 25° C.

Low-viscosity phenylsilicone oils that can be used in accordance with the present disclosure include the oils DC556 (22.5 cSt), SF558 (10-20 cSt) from Dow Corning, Abil AV8853 (4-6 cSt) from Goldschmidt, Silbione 70 633 V 30 (28 cSt) from Rhône Poulenc, 15 M 40 (50 to 100 cSt), 15 M 50 (20 to 25 cSt) from PCR, SF 1550 (25 cSt), PK 20 (20 cSt) from Bayer, Belsil PDM 200 (200 cSt) and Belsil PDM 20 (20 cSt) from Wacker, and KF 53 (175 cSt), KF 54 (400 cSt) and KF 56 (14 cSt) from Shin-Etsu.

The high-viscosity phenylsilicone oil may be present in the composition in an amount ranging from 5 to 99% of the total weight of the composition, for example from 7.5 to 80%, and further, for example, from 10 to 60%, and still further, for example, from 20 to 50%.

The low-viscosity phenylsilicone oil (if present) may be present in the composition in an amount ranging from 5 to 99% of the total weight of the composition, for instance from 7.5 to 80%, for example from 10 to 60% and for example from 10 to 40%.

The ratio by weight between the low-viscosity phenylsilicone oil and the high-viscosity phenylsilicone oil may range, for example from 1/10 to 10/1, for example from 2/10 to 10/2, for example from 3/10 to 10/5. According to one aspect of the present disclosure, this ratio by weight is 1/3.

The composition according to the present disclosure may further comprise at least one non-volatile hydrocarbon oil having a molecular mass of more than 500 g/mol, for example more than 600 g/mol, and for example more than 650 g/mol but not exceeding 15 000 g/mol and/or having a refractive index of more than 1.440 at 20° C. (the refractive index being measured in a refractometer), suitably more than 1.450, and for example more than 1.460.

A "hydrocarbon" compound is a compound comprising principally atoms of carbon and hydrogen and optionally one or more functional groups chosen from hydroxyl, ester, ether and carboxyl functions. These compounds are, according to one aspect, devoid of —Si—O— groups.

The at least one non-volatile hydrocarbon oil may be selected from:
lipophilic polymers such as:
polybutylenes, such as Indopol H-100 (of molar mass or MM=965 g/mol), Indopol H-300 (MM=1 340 g/mol), and Indopol H-1500 (MM=2 160 g/mol), which are sold or manufactured by Amoco;
hydrogenated polyisobutylenes, such as Panalane H-300 E, sold or manufactured by Amoco (M=1 340 g/mol, refractive index: 1.498), Viseal 20000 sold or manufactured by Synteal (MM=6 000 g/mol), and Rewopal PIB 1000, sold or manufactured by Witco (MM=1 000 g/mol);
polydecenes and hydrogenated polydecenes, such as Puresyn 10 (MM=723 g/mol); and Puresyn 150 (MM=9 200 g/mol) sold or manufactured by Mobil Chemicals;
esters such as
linear fatty acid esters having a total carbon number ranging from 30 to 70, such as pentaerythrityl tetrapelargonate (MM=697.05 g/mol);
hydroxy esters, such as diisostearyl malate (MM=639 g/mol, refractive index: 1.462);
aromatic esters such as tridecyl trimellitate (MM=757.19 g/mol);
esters of C24-C28 branched fatty acids or fatty alcohols, such as those described in EP-A-0 955 039, for example triisocetyl citrate (MM=856 g/mol), pentaerythrityl tetraisononanoate (MM=697.05 g/mol), glyceryl triisostearate (MM=891.51 g/mol), glyceryl 2-tridecyltetradecanoate (MM=1 143.98 g/mol), pentaerythrityl tetraisostearate (MM=1 202.02 g/mol), poly-2-glyceryl tetraisostearate (MM=1 232.04 g/mol) or else pentaerythrityl 2-tetradecyltetradecanoate (MM=1 538.66 g/mol);
oils of plant origin such as sesame oil (820.6 g/mol);
and mixtures thereof.

The at least one non-volatile hydrocarbon oil can be suitably selected from linear fatty acid esters having a total carbon number ranging from 30 to 70, hydroxy esters, aromatic esters, esters of C24-C28 branched fatty acids or fatty alcohols, and mixtures thereof.

The at least one non-volatile hydrocarbon oil can also be suitably selected from linear fatty acid esters polyesters of fatty alcohols and polyacids with or without hydroxyl groups, and mixtures thereof.

For example, the at least one non-volatile hydrocarbon oil is selected from hydroxyl-containing polyesters, such as polyesters of fatty monoalcohols and hydroxyl-containing polycarboxylic acids. The fatty monoalcohol suitably comprises from 16 to 22 carbon atoms and the polycarboxylic acid can be, for example, a dicarboxylic acid.

The non-volatile hydrocarbon oil may be present in the composition in an amount ranging from 5 to 99%, for example from 10 to 60%, and for example from 15 to 50%, relative to the total weight of the composition.

The composition according to the disclosure may alsocomprise at least one rheological agent that structures its physiologically acceptable medium.

The at least one rheological agent is capable of thickening and/or gelling the composition. It may be present in an amount effective for increasing the viscosity of the composition, such as to the point where a solid gel is obtained, which is a product which does not flow under its own weight. In this way it is possible to obtain a stick.

The at least one rheological agent can be suitably selected from waxes, fatty compounds that are paste-like at ambient temperature (25° C.), lipophilic gelling agents, and mixtures thereof.

The rheological agent may be present in the composition in an amount ranging from 0.1 to 65%, by weight, for example from 1 to 50%, for example from 3 to 40%, and for example from 5 to 30%, relative to the total weight of the composition.

A "wax" for the purposes of the present disclosure is a lipophilic fatty compound that is solid at ambient temperature (25° C.) and changes from the solid to the liquid state reversibly, having a melting temperature of more than 30° C. and for exmaple more than 45° C., which can be as high as 150° C., a hardness of more than 0.5 MPa at ambient temperature, and an anisotropic crystalline organization in the solid state. By taking the wax to its melting temperature it is possible to make it miscible with the oils and to form a microscopically homogeneous mixture, but, by returning the temperature of the mixture to ambient temperature, the wax is recrystallized in the oils of the mixture.

Waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST 2T-4S, and mixtures thereof.

The at least one rheological agent can suitably comprise a mixture of microcrystalline wax and silicone wax, such as alkyldimethicone wax having a C30-C45 alkyl chain.

The wax or waxes may be present in an amount ranging from 0.1 to 50% by weight relative to the total weight of the composition, for example from 1 to 30%, and for example from 3 to 25%.

The at least one rheological agent may also be a fatty compound that is pastelike at ambient temperature (25° C.). A "fatty compound which is pastelike" means a fatty substance that has a hardness, measured at ambient temperature, ranging from 0.001 to 0.5 MPa, for example from 0.005 to 0.4 MPa. A paste also has a melting point ranging from 20 and 60° C., for example from 25 to 45° C.

A paste-like compound is a viscous product comprising a solid fraction and a liquid fraction.

These fatty substances may suitably be hydrocarbon compounds, optionally polymeric in nature; they may also be selected from silicone compounds and/or fluoro compounds; they may likewise be present in the form of a mixture of hydrocarbon and/or silicone and/or fluoro compounds. In the case of a mixture of different paste-like fatty substances it is possible to use the pastelike hydrocarbon compounds in majority proportion.

Pastelike compounds suitable for use in the composition according to the disclosure herein include lanolins and lanolin derivatives such as acetylated lanolins, magnesium lanolate or oxypropylenated lanolins and mixtures thereof. It is also possible to use esters of fatty acids or fatty alcohols, such as those having 20 to 65 carbon atoms (with a melting point of the order of 20 to 35° C.), such as triisostearyl citrate, arachidyl propionate, and polyvinyl laurate; cholesterol esters; triglycerides of plant origin such as hydrogenated vegetable oils, viscous polyesters such as poly(12-hydroxystearic) acid and mixtures thereof. Triglycerides of plant origin which can be used include derivatives of hydrogenated castor oil, such as Thixinr from Rheox, or else the mixture of triglycerides of lauric, myristic, palmitic and stearic acids which is manufactured or sold under the reference Softisan 100 by Sasol.

Mention may also be made of silicone paste-like fatty substances, such as polydimethylsiloxanes (PDMS) having pendant chains of the alkyl or alkoxy type having 8 to 24 carbon atoms, and a melting point of 20-55° C., such as stearyl dimethicones, for instance those sold by Dow Corning under the trade names DC2503 and DC25514, and mixtures thereof.

The pastelike fatty substance or substances may be present in an amount ranging from 0.1 to 60% by weight relative to the total weight of the composition, for example ranging from 1 to 45% by weight, and for example ranging from 2 to 30% by weight in the composition, when they are present.

The lipophilic gelling agent may be organic or mineral, polymeric or molecular. As mineral lipophilic gelling agents, non-limiting mention may be made of optionally modified clays, such as hectorites modified with a $C_{10}$ to $C_{22}$ fatty acid ammonium chloride, such as hectorite modified with distearyldimethylammonium chloride; pyrogenic silica, optionally having received a hydrophobic surface treatment, whose particle size is less than 1 μm. Polymeric organic lipophilic gelling agents are, for example, partly or totally crosslinked elastomeric organopolysiloxanes, of three-dimensional structure, such as those sold under the names KSG6, KSG16, and KSG18 by Shin-Etsu, Trefil E-505C or Trefil E-506C by Dow Corning, Gransil SR-CYC, SR DMF10, SR-DC556, SR 5CYC gel, SR DMF 10 gel, and SR DC 556 gel by Grant Industries, and SF 1204 and JK 113 by General Electric; ethylcellulose, such as those sold under the name Ethocel by Dow Chemical; copolymers of a $C_{36}$ diacid condensed with ethylenediamine, with a weight-average molecular mass of approximately 6 000, such as the compounds sold by Arizona Chemical under the names Uniclear 80 and Uniclear 100, gums, for instance, silicone gums, such as the PDMS, having a viscosity>100 000 centistokes, galactomannans comprising from one to six, for example from two to four, hydroxyl groups per saccharide unit, substituted by saturated or unsaturated alkyl chain, such as guar gum alkylated with $C_1$ to $C_6$, for example $C_1$ to $C_3$ alkyl chains, and mixtures thereof.

As suitable non-limiting examples of lipophilic gelling agents, mention may be made of non-polymeric, molecular organic gelling agents, also referred to as organogellers, which are compounds whose molecules are capable of establishing physical interactions between themselves that lead to self-aggregation of the molecules, with formation of a 3D supramolecular network, which is responsible for gelling the liquid fatty phase.

A "liquid fatty phase" for the purposes of the present disclosure is a fatty phase which is liquid at ambient temperature (25° C.) and atmospheric pressure (760 mm Hg or 105 Pa), and is composed of one or more fatty substances which are liquid at ambient temperature, also called oils, which are generally mutually compatible. According to one aspect of the disclosure, this liquid fatty phase is composed of the non-volatile hydrocarbon oils described above.

The supramolecular network may result from the formation of a network of fibrils (which are due to stacking or aggregation of organogeller molecules), which immobilizes the molecules of the liquid fatty phase.

The aptitude to form this network of fibrils, and hence to gel, depends on the nature (or chemical class) of the organogeller, on the nature of the substituents carried by its molecules for a given chemical class, and on the nature of the liquid fatty phase.

The physical interactions are diverse but exclude co-crystallization. These physical interactions are, for example, interactions of the self-complementary hydrogen interaction type, π interactions between unsaturated rings, dipolar interactions, coordination bonds with organometallic derivatives, and combinations thereof. Generally speaking, each molecule of an organogeller is able to establish a number of types of physical interaction with a neighboring molecule. Also, the molecules of the organogellers according to the present disclosure may suitably include at least one group that is capable of establishing hydrogen bonds and, for example, at least two groups which are capable of establishing hydrogen bonds, at least one aromatic ring, for example, at least two aromatic rings, at least one or more ethylenically unsaturated bonds and/or at least one or more asymmetric carbons. The groups capable of forming hydrogen bonds are suitably selected from hydroxyl, carbonyl, amine, carboxylic acid, amide, urea and benzyl groups, and combinations thereof.

The at least one organogeller according to the present disclosure is soluble in the liquid fatty phase after heating to the point where a transparent, homogeneous liquid phase is obtained. The at least one organogeller may be solid or liquid at ambient temperature and atmospheric pressure.

The at least one molecular organogeller that can be used in the composition according to the present disclosure include, for example, those described in "Specialist Surfactants" edited by D. Robb, 1997, pp. 209-263, chapter 8 by P. Terech, European applications EP-A-1068854 and EP-A-1086945, or else in application WO-a-02/47031.

Among these organogellers, mention may be made of the amides of carboxylic acids, for example tricarboxylic acids, such as cyclohexanetricarboxamides (see European patent application EP-A-1068854), diamides having hydrocarbon chains each ranging from 1 to 22 carbon atoms, for example from 6 to 18 carbon atoms, the said chains being unsubstituted or substituted by at least one substituent selected from ester, urea and fluoro groups (see application EP-A-1086945), and suitably diamides resulting from the reaction of diaminocyclohexane, including diaminocyclohexane in trans form, with an acid chloride such as, for example, N,N'-bis(dodecanoyl)-1,2-diaminocyclohexane, amides of N-acylamino acids, such as the diamides resulting from the reaction of an N-acylamino acid with amines comprising from 1 to 22 carbon atoms, such as, for example, those described in WO-93/23008, and for example the amides of N-acylglutamic acid in which the acyl group may be chosen from $C_8$ to $C_{22}$ alkyl chains, such as the dibutyl amide of N-lauroyl-L-glutamic acid, which is sold or manufactured by Ajinomoto under the name GP-1, and mixtures thereof.

The lipophilic gelling agent may be present in an amount ranging from 0.1 to 50% by weight, for example from 1 to 30% by weight, and for example from 2 to 20% by weight, relative to the total weight of the composition.

The particulate phase present in the composition according to the present disclosure may comprise pigments and/or nacres and/or fillers which are commonly used in cosmetic compositions.

The particulate phase may be present in an amount ranging from 0.01 to 60%, for example from 10 to 25% by weight, relative to the total weight of the composition.

According to the present disclosure, the rheological agent is distinct from the particulate phase and for example from the filler or fillers optionally present in the particulate phase.

Pigments are to be understood as particles, which are insoluble in the fatty substances such as oils and which are intended for colouring and/or opacifying the composition. Fillers should be understood as meaning particles that may be colourless, white, mineral, synthetic, and which may be lamellar or non-lamellar. Nacres or nacreous pigments should be understood as meaning iridescent particles, produced for example by certain molluscs in their shell, or else synthesized.

The pigments may be white or coloured, mineral and/or organic, coated or uncoated, and spherical or oblong. Non-limiting examples of mineral pigments include titanium dioxide, optionally surface-treated, zirconium oxide or cerium oxide, and zinc oxide, iron oxide (black, yellow, brown or red) or chromium oxide, manganese violet, ultramarine blue, chromium hydrate and Prussian blue. Non-limiting examples of organic pigments include carbon black, organic lake-type pigments of barium, strontium, calcium or aluminium or else lakes based on cochineal carmine. The pigments may be present in the composition in an amount ranging from 0.05 to 40% of the weight of the final composition, for example ranging from 2 to 20% for a non-pulverulent composition.

The nacres or nacreous pigments may be selected from white nacreous pigments such as mica, covered with titanium or with bismuth oxychloride, coloured nacreous pigments such as titanium mica with iron oxides, titanium mica with, for example, Prussian blue or chromium oxide, titanium mica with an organic pigment of the aforementioned type, and nacreous pigments based on bismuth oxychloride. It is also possible to use pigments having goniochromatic properties, especially liquid-crystal pigments or multilayer pigments. The nacres may be present in the composition in an amount ranging from 0.01 to 20% of the total weight of the composition, for example ranging from 1 to 15%.

The fillers may be present in an amount ranging from 0.01 to 35% by weight (if present) relative to the total weight of the composition, for example 0.5 to 15%. Of examples of fillers, non-limiting mention may be made of talc, mica, kaolin, lauroyllysine, polyamide powders such as Nylon® (for example Orgasol) and polyethylene powders, polytetrafluoroethylene (Teflon®) powders, starch, boron nitride, copolymer microspheres such as Expancel® (Nobel Industrie), Polytrap® (Dow Corning), Polypore® L 200 (Chemdal Corporation) and silicone resin microbeads (Tospearl® from Toshiba, for example).

The composition of the disclosure may contain little or no volatile oils, for example less than 10% by weight, relative to the total weight of the composition, for example less than 5%, and for example less than 2%. According to one aspect of the disclosure the composition is free from volatile oil.

The composition according to the present disclosure may further comprise at least one additional non-aqueous compound other than the phenylsilicone oil and the non-volatile hydrocarbon oil having a molecular mass of more than 500 g/mol, the said compound being selected from oils, gums, resins, lipophilic polymers and mixtures thereof.

The gums which can be used in accordance with the present disclosure may be present in a form in which they are solubilized in an oil, and the resins may be liquid or solid at ambient temperature. The nature and amount of the gums and resins are a function of the desired textures and mechanical properties.

The additional oils may be hydrocarbon and/or silicone and/or fluoro oils. These oils may be animal, vegetable, mineral or synthetic in origin. Possible examples of additional oils that can be used in accordance with the present disclosure include:

hydrocarbon oils of animal origin, such as perhydrosqualene;

vegetable hydrocarbon oils, such as liquid triglycerides of fatty acids comprising from 4 to 10 carbon atoms, such as the triglycerides of heptanoic or octanoic acid or jojoba oil;

linear or branched hydrocarbons of mineral or synthetic origin, such as liquid paraffins and their derivatives, and petroleum jelly;

synthetic esters and ethers, for example those of fatty acids, such as the oils of formula $R_1COOR_2$ wherein $R_1$ represents the residue of a higher fatty acid comprising from 1 to 40 carbon atoms and $R_2$ represents a hydrocarbon chain comprising from 1 to 40 carbon atoms, where $10 \leq R_1+R_2 \leq 41$, such as, for example, isopropyl myristate, 2-ethylhexyl palmitate, 2-octyldodecyl stearate and 2-octyldodecyl erucate;

fatty alcohols comprising from 12 to 26 carbon atoms, such as octyldodecanol, 2-butyloctanol, 2-hexyldecanol, 2-undecylpentadecanol and oleyl alcohol;

$C_8$-$C_{26}$ higher fatty acids, such as oleic acid, linoleic acid, linolenic acid or isostearic acid;

fluoro oils optionally with a partial hydrocarbon and/or silicone fraction;

silicone oils such as volatile or non-volatile, linear or cyclic polydimethylsiloxanes (PDMS); polydimethylsiloxanes comprising alkyl or alkoxy groups having 2 to 24 carbon atoms, pendantly or at the end of the silicone chain;

and mixtures thereof.

The composition of the present disclosure may further comprise at least one additive commonly used in the cosmetic compositions, such as water, dyes, aromas, fragrances, antioxidants, preservatives, neutralizing agents, aqueous-phase gelling agents, dispersants, cosmetic actives, and mixtures thereof. If the selected additive is water, it may be present in an amount ranging from 0.01 to 80% by weight and, for example, from 1 to 70% and for example from 1 to 60%, relative to the total weight of the composition. If the selected additives are other than water, the additive may be present in the composition in an amount ranging from 0.0005 to 20% by weight, relative to the total weight of the composition, for example from 0.001 to 10%.

A "cosmetic active" is a lipophilic or hydrophilic compound that provides benefit to the keratin materials, for example the skin and the lips. Cosmetic actives that can be used in accordance with the present disclosure include vitamins A, E, C, $B_3$ and F, provitamins such as D-panthenol, soothing actives such as α-bisabolol, aloe vera, allantoin, plant extracts or essential oils, protectives or restructuring agents such as ceramides, freshness actives such as menthol and its derivatives, emollients (cocoa butter, dimethicone), moisturizers (arginine PCA), antiwrinkle actives, essential fatty acids, sunscreens, and mixtures thereof.

The person of ordinary skill in the art will of course take care to select any complementary additives and/or their amount in such a way that the beneficial properties of the composition according to the present disclosure are not, or not substantially, adversely affected by the intended addition.

The applications of the composition according to the present disclosure are manifold and relate to all cosmetic products, whether coloured or otherwise, and for example to lip makeup products such as lipsticks or lip glosses or else lip pencils.

In accordance with one aspect of the present disclosure, the composition according to the present disclosure may be in the form of a cast product, and for example in the form of a stick, or in the form of a dish which can be used by direct contact or with a sponge, or else in a heating bag. For example, it may be in solid form and in that case is employed as a cast foundation, cast blusher or eyeshadow, lipstick, lipcare base or balm, or concealer product. It may also be in the form of a liquid foundation or lipstick, a lip gloss, a suncare product or a skin colouring product.

The composition in accordance with the present disclosure may be anhydrous and may contain less than 5% of added water relative to the total weight of the composition. In that case it may be present for example in the form of an oily gel, oily liquid, anhydrous paste or stick that comprises for example a vesicular dispersion of ionic and/or non-ionic lipids.

It may also be present in the form of a single or multiple emulsion with a continuous oily or aqueous phase, or in the form of an oily dispersion in an aqueous phase, brought about by virtue of vesicles comprising ionic and/or non-ionic lipids. These formulations are prepared in accordance with methods customary in the fields in question.

The composition according to the present disclosure may be present in the form of a coloured or non-coloured skincare composition, in the form of a sun protection composition or makeup remover composition, or else in the form of a hygiene composition. If it includes cosmetic actives, it may then be used as a non-therapeutic treatment or care base for the skin, such as the hands or face, or for the lips (lip balms, protecting the lips from cold and/or sun and/or wind) or as an artificial tanning product.

The composition in accordance with the present disclosure may also be present in the form of a coloured skin-makeup product, for example a face makeup product such as a rouge, a blusher or eyeshadow, a body makeup product such as a semi-permanent tattooing product or a lip makeup product such as a lipstick or lip gloss, possibly having non-therapeutic treatment or care properties, a product for making up the exoskeletal appendages, such as, for example, a nail varnish, a mascara, an eyeliner or a haircare or hair colouring product.

The composition according to the present disclosure may be in the form of a lip makeup product, such as a lipstick or a lip gloss.

A lip makeup product is present suitably in anhydrous form.

The composition of the present disclosure is, of course, be physiologically acceptable: that is, non-toxic and capable of being applied to the skin (including the inside of the eyelids), the lips or the exoskeletal appendages of human beings. It can be cosmetically acceptable: that is, pleasant in taste, feel, appearance and/or odour, and capable of being applied several times a day for a number of months.

The composition according to the present disclosure may be manufactured by known processes which are generally used in the cosmetics field.

The aim of the examples that follow is to give non-limiting illustrations of the subject-matter of the present invention. The amounts are given as percentages by mass.

EXAMPLES 1 TO 4

Comparative Tests—Lipsticks

The compositions featured in Table (1) below are as follows:

the composition of Example 1 comprised a silicone oil, cyclopentasiloxane;

the composition of Example 2 comprised a volatile hydrocarbon oil, isododecane, with a molecular mass of 170 g/mol;

the composition of Example 3 comprised a non-volatile hydrocarbon oil, isononyl isononanoate, having a molecular mass of 284 g/mol and a refractive index of 1.436;

the composition of Example 4 according to the present disclosure comprised diisostearyl malate having a molecular mass of 639 g/mol and a refractive index of 1.462.

TABLE (1)

| Phase | | Example 1 (comparative) | Example 2 (comparative) | Example 3 (comparative) | Example 4 (inventive) |
|---|---|---|---|---|---|
| A | Cyclopentasiloxane | 30 | | | |
| | Isododecane | | 30 | | |
| | Isononyl isononanoate | | | 30 | |
| | Diisostearyl malate | | | | 30 |
| | Phenyltrimethyltrisiloxane (20 cSt) manufactured or sold by Dow Corning as DC 556 | 18 | 18 | 18 | 18 |
| | Phenyltrimethyltrisiloxane (1 000 cSt) manufactured or sold by Wacker as Belsil PDM 1000 | qs 100 | qs 100 | qs 100 | qs 100 |
| B | Microcrystalline wax | 10 | 10 | 10 | 10 |
| | $C_{30}$-$C_{45}$ alkyldimethicone | 2.5 | 2.5 | 2.5 | 2.5 |
| | Mixture of triglycerides of lauric, myristic, palmitic and stearic acids (50/20/10/10) manufactured or sold as Softisan 100 by Sasol | 10 | 10 | 10 | 10 |
| C | Red 7 | 0.26 | 0.26 | 0.26 | 0.26 |
| | Red 21 | 0.06 | 0.06 | 0.06 | 0.06 |
| | Black iron oxide | 0.09 | 0.09 | 0.09 | 0.09 |
| | Brown iron oxide | 2.1 | 2.1 | 2.1 | 2.1 |
| | Titanium oxide mica | 1.8 | 1.8 | 1.8 | 1.8 |

Procedure

The pigments (Phase C) wee ground in the diisostearyl malate of Phase A and the ground product was then mixed with Phase B (waxes and pastes) and with the remainder of Phase A. The mixture was heated in a jacketed pot for at least 30 minutes after the waxes had totally melted.

The resultant paste was cast in a mould appropriate for sticks, which was heated at 40-42° C. and then held at −18° C. for half an hour. The sticks were then demoulded.

Cosmetic Evaluation

The 4 lipsticks were evaluated by 5 qualified persons according to various criteria.

The sticks of Examples 2 and 3 were judged to have poor deposition properties owing to an excessively soft consistency; the stick of Example 1 was adjudged to deposit well on the lips but to exhibit a loss of gloss over time. The stick of Example 4 according to the present disclosure was adjudged to deposit well and the film of composition was adjudged to be homogeneous and glossy.

EXAMPLE 5

Lipstick

| Phase | | |
|---|---|---|
| A | Diisostearyl malate | qs 100 |
| | Phenyltrimethyltrisiloxane (20 cSt) manufactured or sold by Dow Corning as DC 556 | 18 |
| | Phenyltrimethyltrisiloxane (1 000 cSt) manufactured or sold by Wacker as Belsil PDM 1000 | 27 |
| B | Microcrystalline wax | 10 |
| | C30-C45 alkyl dimethicone | 2.5 |
| | Mixture of triglycerides of lauric, myristic, palmitic and stearic acids (50/20/10/10) sold or manufactured as Softisan 100 by Sasol | 10 |
| C | Red 7 | 0.26 |
| | Red 21 | 0.06 |
| | Black iron oxide | 0.09 |
| | Brown iron oxide | 2.1 |
| | Titanium oxide mica | 1.8 |

The procedure was the same as that of Examples 1 to 4.

Cosmetic Evaluation

The staying power of this composition was evaluated using instrumental and sensorial methods on a panel of 12 qualified persons, who applied the lipstick.

The staying power was evaluated as follows:

in the first phase, an evaluation of the overall "sensorial" staying power is carried out one hour after application of the formula to the lips.

in the second phase, an "instrumental" staying power was evaluated after a series of tests, which consist in making two "bites" on a paper tissue, drinking a hot drink and then a cold drink and eating 4 bites of a sandwich and of an apple.

The sensorial staying power was evaluated on a scale from 1 to 10:1 corresponds to a formula which has no staying power at all and 10 to a formula whose staying power is very good.

The instrumental staying power was evaluated on a scale from 1 to 100:1 corresponds to a formula that has no staying power at all and 100 to a formula whose staying power is very good.

The gloss and comfort were also evaluated by these 12 individuals:

the gloss was evaluated just after the application of the formula and then after one hour (the instrumental gloss was evaluated on a scale ranging from 1 to 200. 1 corresponds to a formula which is not glossy at all and 200 to a very glossy formula.)

The instrumental gloss was measured with the aid of a gloss meter, conventionally, by the following method.

A Leneta contrast chart referenced Form 1A Penopac was spread with a 50 μm layer of the composition whose average gloss is to be evaluated, using an automatic spreader. The layer covers at least the white background of the chart. Then the gloss was measured at 20° on the white background using a Byk-Gardner microTri-Gloss gloss meter.

the comfort was evaluated after one hour.

| Results | | | | |
|---|---|---|---|---|
| | | Staying power | Gloss | Comfort |
| Sensorial evaluation | On application | | 6.3 | |
| | After 1 hour | 6.4 | 4.8 | 7.4 |
| Instrumental evaluation | On application | | 171 | |
| | After 1 hour | 82 | 138 | |
| | After tests | 54 | | |

The composition had good cosmetic properties, in particular of gloss and comfort, and its staying power over time was highly satisfactory.
The application (ease of application and lubricity) of the film of composition was also adjudged to be satisfactory.

What is claimed is:

1. A cosmetic composition in the form of a lip makeup product comprising, in a physiologically acceptable medium, at least one high viscosity phenylsilicone oil having a viscosity greater than or equal to 500 cSt in an amount ranging from 5 to 60%,
   at least one non-volatile ester oil having a molecular mass of more than 500 g/mol chosen from pentaerythrityl tetrapelargonate, diisostearyl malate, tridecyl trimellitate, triisocetyl citrate, pentaerythrityl tetraisononanoate, glyceryl triisostearate, glyceryl 2-tridecyl tetradecanoate, and pentaerythrityl tetraisostearate,
   at least one rheological agent,
   at least one low viscosity phenylsilicone oil having a viscosity of less than 500 cst, and
   a particulate phase,
   wherein the composition contains less than 5% by weight, relative to the total weight of the composition, of a volatile oil,
   wherein the at least one high viscosity phenylsilicone oil is chosen from the oils of formula (A):

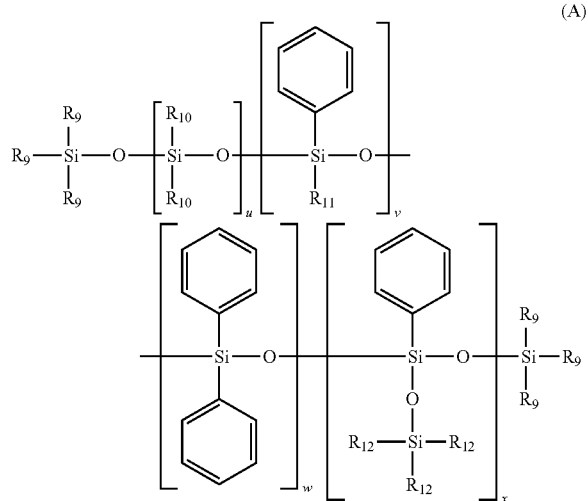

(A)

wherein:
   $R_9$ and $R_{12}$, which may be identical or different, are chosen from $C_1$-$C_{30}$ alkyl radicals, aryl radicals, and aralkyl radicals,
   $R_{10}$ and $R_{11}$, which may be identical or different, are chosen from $C_1$-$C_{30}$ alkyl radicals and aralkyl radicals, u, v, w and x, which may be identical or different, are integers ranging from 0 to 900,
with the provisos that the sum of v+w+x is other than 0, and that the sum of u+v+w+x ranges from 151 to 900.

2. The composition according to claim 1, wherein the at least one non-volatile ester oil is present in an amount ranging from 5 to 60% by weight, relative to the total weight of the composition.

3. The composition according to claim 2, wherein the at least one non-volatile ester oil is present in an amount ranging from 10 to 60% by weight, relative to the total weight of the composition.

4. The composition according to claim 3, wherein the at least one non-volatile ester oil is present in an amount ranging from 15 to 50% by weight, relative to the total weight of the composition.

5. The composition according to claim 1, wherein the at least one high viscosity phenylsilicone oil has a viscosity at 25° C. ranging from 500 to 10 000 cSt.

6. The composition according to claim 5, wherein the at least one high-viscosity phenylsilicone oil has a viscosity at 25° C. ranging from 600 to 5 000 cSt.

7. The composition according to claim 6, wherein the at least one high viscosity phenylsilicone oil has a viscosity at 25° C. ranging from 600 to 3 000 cSt.

8. The composition according to claim 1, wherein the at least one high viscosity phenylsilicone oil is present in an amount ranging from 20 to 50% by weight, relative to the total weight of the composition.

9. The composition according to claim 1, wherein the at least one low viscosity phenylsilicone oil has a viscosity at 25° C. ranging from 5 to 500 cSt.

10. The composition according to claim 9, wherein the at least one low-viscosity phenylsilicone oil has a viscosity at 25° C. ranging from 5 to 300 cSt.

11. The composition according to claim 10, wherein the at least one low-viscosity phenylsilicone oil has a viscosity at 25° C. ranging from 5 to 100 cSt.

12. The composition according to claim 1, wherein the at least one low-viscosity phenylsilicone oil is chosen from the oils of formula (A):

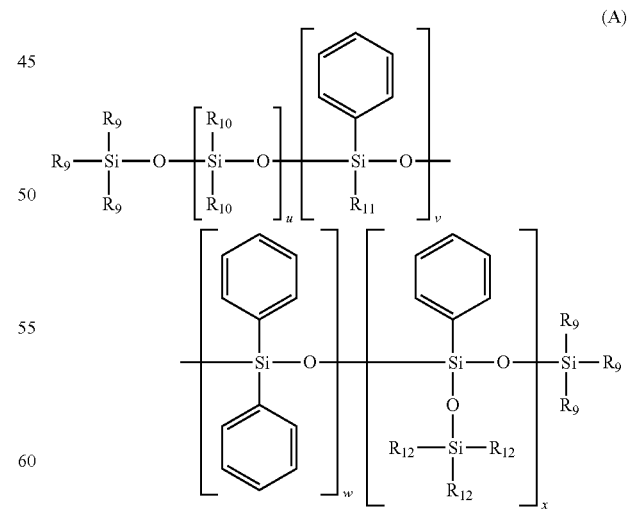

(A)

wherein:
   $R_9$ and $R_{12}$, which may be identical or different, are chosen from $C_1$-$C_{30}$ alkyl radicals, aryl radicals, and aralkyl radicals, $R_{10}$ and $R_{11}$, which may be identical or different, are chosen from $C_1$-$C_{30}$ alkyl radicals and aralkyl radicals, u, v, w and x, which may be identical or different, are integers ranging from 0 to 900, with the provisos that the sum of v+w+x is other than 0, and that the sum of u+v+w+x ranges from 1 to 150.

13. The composition according to claim 1, wherein the at least one low-viscosity phenylsilicone oil is present in an amount ranging from 5 to 80% by weight, relative to the total weight of the composition.

14. The composition according to claim 1, wherein the ratio by weight between the at least one low-viscosity phenylsilicone oil and the at least one high-viscosity silicone oil ranges from 1/10 to 10/1.

15. The composition according to claim 14, wherein the ratio by weight between the at least one low-viscosity phenylsilicone oil and the at least one high-viscosity silicone oil ranges from 2/10 to 10/2.

16. The composition according to claim 15, wherein the ratio by weight between the at least one low-viscosity phenylsilicone oil and the at least one high-viscosity silicone oil ranges from 3/10 to 10/5.

17. The composition according to claim 1, wherein said composition is in anhydrous form.

18. The cosmetic composition comprising according to claim 1, wherein said rheological agent is chosen from silicone waxes.

19. The composition according to claim 18, wherein the at least one non-volatile ester oil is present in an amount ranging from 5 to 60% by weight, relative to the total weight of the composition.

20. The composition according to claim 19, wherein the at least one non-volatile ester oil is present in an amount ranging from 10 to 60% by weight, relative to the total weight of the composition.

21. The composition according to claim 20, wherein the at least one non-volatile ester oil is present in an amount ranging from 15 to 50% by weight, relative to the total weight of the composition.

22. The composition according to claim 18, wherein the at least one high viscosity phenylsilicone oil has a viscosity at 25° C. ranging from 500 to 10 000 cSt.

23. The composition according to claim 22, wherein the at least one high-viscosity phenylsilicone oil has a viscosity at 25° C. ranging from 600 to 5 000 cSt.

24. The composition according to claim 23, wherein the at least one high viscosity phenylsilicone oil has a viscosity at 25° C. ranging from 600 to 3 000 cSt.

25. The composition according to claim 18, wherein the at least one phenylsilicone oil is present in an amount ranging from 20 to 50% by weight, relative to the total weight of the composition.

26. The composition according to claim 18, wherein the at least one low viscosity phenylsilicone oil has a viscosity at 25° C. ranging from 5 to 500 cSt.

27. The composition according to claim 26, wherein the at least one low-viscosity phenylsilicone oil has a viscosity at 25° C. ranging from 5 to 300 cSt.

28. The composition according to claim 27, wherein the at least one low-viscosity phenylsilicone oil has a viscosity at 25° C. ranging from 5 to 100 cSt.

29. The composition according to claim 18, wherein the at least one low-viscosity phenylsilicone oil is selected from the oils of formula (A):

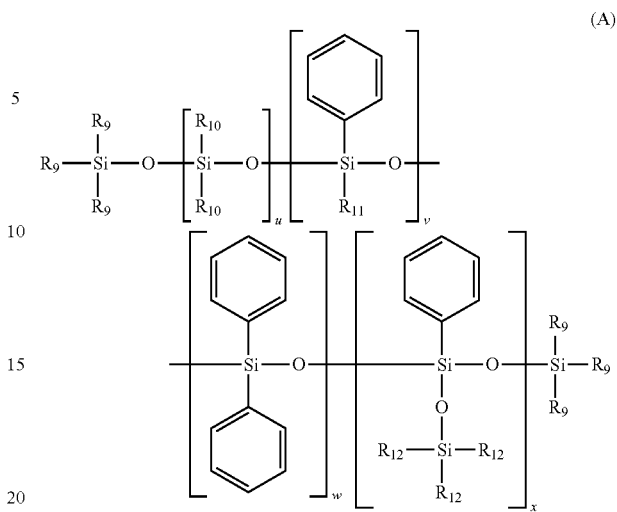

wherein:
$R_9$ and $R_{12}$, which may be identical or different, are chosen from $C_1$-$C_{30}$ alkyl radicals, aryl radicals, and aralkyl radicals, $R_{10}$ and $R_{11}$, which may be identical or different, are chosen from $C_1$-$C_{30}$ alkyl radicals and aralkyl radicals, u, v, w and x, which may be identical or different, are integers ranging from 0 to 900, with the provisos that the sum of v+w+x is other than 0, and that the sum of u+v+w+x ranges from 1 to 150.

30. The composition according to claim 18, wherein the at least one low-viscosity phenylsilicone oil is present in an amount ranging from 5 to 80% by weight, relative to the total weight of the composition.

31. The composition according to claim 18, wherein the ratio by weight between the at least one low-viscosity phenylsilicone oil and the at least one high-viscosity silicone oil ranges from 1/10 to 10/1.

32. The composition according to claim 31, wherein the ratio by weight between the at least one low-viscosity phenylsilicone oil and the at least one high-viscosity silicone oil ranges from 2/10 to 10/2.

33. The composition according to claim 32, wherein the ratio by weight between the at least one low-viscosity phenylsilicone oil and the at least one high-viscosity silicone oil ranges from 3/10 to 10/5.

34. The composition according to claim 1, wherein the at least one rheological agent is present in an amount ranging from 0.1 to 65% by weight, relative to the total weight of the composition.

35. The composition according to claim 34, wherein the at least one rheological agent is present in an amount ranging from 1 to 50% by weight, relative to the total weight of the composition.

36. The composition according to claim 35, wherein the at least one rheological agent is present in an amount ranging from 3 to 40% by weight, relative to the total weight of the composition.

37. The composition according to claim 36, wherein the at least one rheological agent is present in an amount ranging from 5 to 30% by weight, relative to the total weight of the composition.

38. The composition according to claim 18, wherein the silicone waxes are chosen from alkyldimethicones and alkoxydimethicones having an alkyl or alkoxy chain comprising from 10 to 45 carbon atoms, and poly(di)methylsiloxane esters which are solid at 30° C. and whose ester chain comprises at least 10 carbon atoms.

39. The composition according to claim 1, further comprising at least one apolar hydrocarbon wax chosen from paraffin, lignite wax, microcrystalline wax, ceresin, ozokerite, synthetic waxes, and Fischer-Tropsch waxes.

40. The composition according to claim 39, wherein the synthetic waxes are chosen from the polyethylene waxes obtained from the polymerization or copolymerization of ethylene.

41. The composition according to claim 18, wherein said composition is in anhydrous form.

42. The composition according to claim 1, wherein the particulate phase comprises pigments and/or nacres and/or fillers.

43. The composition according to claim 1, wherein the particulate phase is present in an amount ranging from 0.01 to 60% by weight, relative to the total weight of the composition.

44. The composition according to claim 43, wherein the particulate phase is present in an amount ranging from 5 to 25% by weight, relative to the total weight of the composition.

45. A cosmetic process for imparting at least one property chosen from staying power and gloss to a film of a cosmetic composition in the form of a lip make up product comprising a physiologically acceptable medium, comprising introducing into the said composition an effective amount of at least one high viscosity phenylsilicone oil having a viscosity of greater than or equal to 500 cSt in an amount ranging from 5 to 60%, at least one non-volatile ester oil having a molecular mass of more than 600 g/mol chosen from pentaerythrityl tetrapelargonate, diisostearyl malate, tridecyl trimellitate, triisocetyl citrate, pentaerythrityl tetraisononanoate, glyceryl triisostearate, glyceryl 2-tridecyl tetradecanoate, and pentaerythrityl tetraisostearate, at least one rheological agent, at least one low viscosity phenylsilicone oil having a viscosity of less than 500 cst, and a particulate phase, wherein said at least one non-volatile ester oil is soluble or dispersible in the said high viscosity phenylsilicone oil, wherein said composition contains less than 5% by weight, relative to the total weight of the composition, of a volatile oil, wherein the at least one high viscosity phenylsilicone oil is selected from the oils of formula (A):

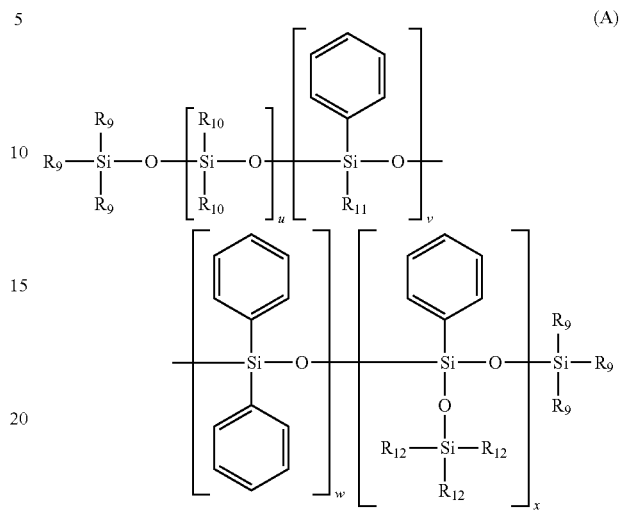

wherein:
- $R_9$ and $R_{12}$, which may be identical or different, are chosen from $C_1$-$C_{30}$ alkyl radicals, aryl radicals, and aralkyl radicals,
- $R_{10}$ and $R_{11}$, which may be identical or different, are chosen from $C_1$-$C_{30}$ alkyl radicals and aralkyl radicals,
- u, v, w and x, which may be identical or different, are integers ranging from 0 to 900, with the provisos that the sum of v+w+x is other than 0, and that the sum of u+v+w+x ranges from 151 to 900.

46. The composition according to claim 1, wherein the at least one ester is diisostearyl malate.

47. The composition according to claim 18, wherein the at least one ester is diisostearyl malate.

* * * * *